(12) United States Patent
Tatsuoka et al.

(10) Patent No.: US 6,624,308 B2
(45) Date of Patent: *Sep. 23, 2003

(54) METHOD OF PRODUCTION AND METHOD OF SEPARATION OF 2,4'-DIPYRIDYL DERIVATIVES AND METHODS OF PRODUCTION OF BENZOXAZEPINE DERIVATIVES AND SALTS THEREOF

(75) Inventors: Toshio Tatsuoka, Nishinomiya (JP); Katsuhide Kamei, Takatsuki (JP)

(73) Assignee: Daiichi Suntory Pharma Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/590,678

(22) Filed: Jun. 9, 2000

(65) Prior Publication Data

US 2003/0125547 A1 Jul. 3, 2003

Related U.S. Application Data

(62) Division of application No. 09/230,168, filed as application No. PCT/JP98/02264 on May 22, 1998, now Pat. No. 6,096,884.

(30) Foreign Application Priority Data

May 22, 1997 (JP) ............................................. 9-132631

(51) Int. Cl.[7] ............................................ C07D 401/00
(52) U.S. Cl. ..................................................... 546/276.4
(58) Field of Search ....................................... 546/276.4

(56) References Cited

FOREIGN PATENT DOCUMENTS

| EP | 0755 930 | 9/1996 |
|---|---|---|
| WO | WO98/52922 | 11/1998 |

OTHER PUBLICATIONS

Preparation of π–Deficient Heteroarylzinc Halides by Oxidative Addition of Active Zinc and Its Palladium–Catalyzed Reaction, (1993), Takao Sakamoto et al.,Tetrahedron vol. 49, No. 43, pp. 9713–9720.
A Novel Synthesis of 4–Aryl– and 4–Heteroarylpyridines via Diethyl(4–pyridy)borane, (1985), Minoru Ishikura et al, Chem. Pharm. Bull., vol. 33, No. 11, pp. 4755–4763.
Synthese von unsymmetrischen und symmetrischen Dihydroxybipyridinen, (1992), Eckehard V. Dehmlow et al., Liebigs Ann. Chem., pp. 953–959. (Article not translated to English).

*Primary Examiner*—Alan L. Rotman
*Assistant Examiner*—Binta Robinson
(74) *Attorney, Agent, or Firm*—Burns, Doane, Swecker & Mathis, LLP

(57) ABSTRACT

A method of production of 2,4'-dipyridyl derivatives by a cross coupling reaction of a 2-halopyridine derivative and a 4-halopyridine using a nickel complex catalyst and a method of separation of a 2,4'-dipyridyl derivative from a mixture of dipyridyl isomers containing a 2,2'-dipyridyl derivative, 2,4'-dipyridyl derivative, and 4,4'-dipyridyl by using a dilute aqueous copper sulfate solution to insolubilize and remove the 2,2'-dipyridyl derivative and 4,4'-dipyridyl are disclosed.

10 Claims, No Drawings

METHOD OF PRODUCTION AND METHOD OF SEPARATION OF 2,4'-DIPYRIDYL DERIVATIVES AND METHODS OF PRODUCTION OF BENZOXAZEPINE DERIVATIVES AND SALTS THEREOF

This application is a divisional, of application Ser. No. 09/230,168, filed Jan. 21, 1999 now U.S. Pat. No. 6,096,884 which application was filed under 35 U.S.C. §371 from PCT/JP98/02264, filed May 22, 1998.

TECHNICAL FIELD

The present invention relates to a method of producing 2,4'-dipyridyl derivatives, a method of separating 2,4'-dipyridyl derivatives, and methods of producing benzoxazepine derivatives and their salts. More specifically, it relates to a method of producing 2,4'-dipyridyl derivatives by a cross coupling reaction of halopyridines, a method of separating a 2,4'-dipyridyl derivative from a dipyridyl derivative isomer mixture containing the 2,4'-dipyridyl derivative, and methods of producing benzoxazepine derivatives and their salts using the above methods.

BACKGROUND ART

Various reports have been made up to now on methods for synthesis of 2,4'-dipyridyl, but all of these methods of synthesis involve problems. None of the methods of synthesis are satisfactory.

For example, in the condensation reaction of 4-cyanopyridine and acetylene disclosed in the specification of U.S. Pat. No. 4,196,287, there is the danger of explosion since a high pressure acetylene gas is used, and therefore, special equipment is required, and the method is not generally accepted.

Further, in the Ullmann-like reaction of 2-halopyridine and 4-halopyridine (Khim. Geol. Nauk., vol. 5, p. 114, 1970), 2,2'-dipyridyl and 4,4'-dipyridyl are produced, in addition to the desired 2,4'-dipyridyl, and therefore, the yield is poor.

Further, cross coupling reactions between a halopyridine and various pyridine metal reagents (see Grignard reagent: Synthesis, vol. 7, p. 564, 1986; tin reagents: T. L., vol. 33, no. 16, p. 2199, 1992; borane reagent: Chem. Pharm. Bull., vol. 33, no. 11, p. 4755, 1985) using a palladium catalyst has been reported in numerous conditions, but isomers such as 2,2'-dipyridyl and 4,4'-dipyridyl are produced in large amounts in addition to the desired 2,4'-dipyridyl, and therefore, the yield is poor and the purification is very tedious.

Further, as another method, the reaction with an N-ethoxycarbonyl pyridinium salt (see J. Chin. Chem. Soc. (Taipei), vol. 36, no. 6, p. 609, 1989) was reported, but the yield is extremely poor and in the improved method (see Heterocycle, vol. 31, no. 4, p. 637, 1990), the number of reaction steps is tremendously increased, and therefore, this method is not practical.

There have been other methods reported in literature, but the synthetic routes are long and the yields of all of the processes are low (for example, see T.L., vol. 25, no. 35, p. 3887, 1994 and Pol. J. Chem., vol. 53, no. 4, p. 893, 1979).

As explained above, all of the reported methods of 2,4'-dipyridyl up to now have been poor in yield or have not been easy in operation and were not industrially satisfactory. Further, the simple removal method of the isomers, i.e., 2,2'-dipyridyl or 4,4'-dipyridyl, which were sometimes produced has not been studied at all.

DISCLOSURE OF INVENTION

The object of the present invention is to provide a method of producing 2,4'-dipyridyl derivatives which is good in yield, easy in operation, and industrially satisfactory and a simple method for separating the 2,4'-dipyridyl derivatives from a mixture of dipyridyl derivative isomers.

Another object of the present invention is to provide an industrially satisfactory method of producing benzoxazepine derivatives and the salts thereof, using the above method.

The present inventors engaged in intensive studies in consideration of the above situation with the intent of establishing a method for the industrial production of 2,4'-dipyridyl derivatives and easy separation and refinement of its isomers as a result found that with a coupling reaction between a 2-halopyridine derivative of the formula (I):

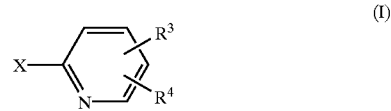

(I)

wherein X represents a halogen atom and $R^3$ and $R^4$ independently represents a hydrogen atom, a halogen atom, or a $C_1$–$C_4$ lower alkyl group and 4-halopyridine is carried out using a nickel complex catalyst, a 2,4'-dipyridyl derivative is simply obtained with a good yield and, further due to the difference in chelating abilities among dipyridyl isomers, the process of separation and purification of the desired 2,4'-dipyridyl derivative from the byproduct 2,2'-dipyridyl derivative and 4,4'-dipyridyl, can be effected by using copper sulfate to insolubilize the by-products as copper salts, whereby the present invention has been completed.

In the present invention, in the above general formula (I), when X is Cl, $R^3$ and $R^4$ are preferably F as halogen atoms and are preferably methyl groups and ethyl groups as the lower alkyl groups. In the most preferable combination of $R^3$ and $R^4$, $R^3$ and $R^4$ are the same and are hydrogen atoms. According to the present invention, by using a 2-halopyridine derivative and 4-halopyridine as the starting materials, using the nickel complex catalyst used for homoaryl coupling (J. Organomet., Chem., 1971, vol. 28, p. 287), and performing a coupling reaction in the presence of zinc and a tetraalkylammonium halide salt, a 2,4'-dipyridyl derivative can be obtained with a good yield in a single step.

Further, depending on the reaction conditions, in addition to the 2,4'-dipyridyl derivative, small amounts of 2,2'-dipyridyl derivative or 4,4'-dipyridyl may be produced as by-products. The separation of only the 2,4'-dipyridyl derivative from the mixture of these dipyridyl isomers can be achieved as follows. Due to the difference in the chelating ability among dipyridyl isomers, it has been found that, by dissolving the mixture of the dipyridyl derivative isomers in an organic solvent, followed by adding a dilute copper sulfate solution, then stirring, the 2,2'-dipyridyl derivative and 4,4'-dipyridyl formed copper salts and precipitated as insolubles. By filtering out these insolubles using Celite etc., it is possible to obtain just the desired 2,4'-dipyridyl derivative in the organic solvent layer. By condensing this organic layer under reduced pressure, only the pure 2,4'-dipyridyl derivative can be obtained.

Further, according to this method, benzoxazepine derivatives and its salts can be industrially advantageously obtained.

BEST MODE FOR CARRYING OUT THE INVENTION

I. Method of Production of 2,4'-Dipyridyl Derivatives

The 2-halopyridine derivative capable of being used in the method of production of a 2,4'-dipyridyl derivative by a coupling reaction of the present invention is a 2-bromopyridine derivative or a 2-chloropyridine derivative. The 4-halopyridine is 4-bromopyridine or 4-chloropyridine. These may be added to the reaction mixture as free amines or pyridinium salts, or added after being neutralized by an amine in an organic solvent.

The molar ratio of the 2-halopyridine derivative and the 4-halopyridine is preferably 4:1 to 1:4, more preferably 1:1. Even if the amount of 2-halopyridine is present in excess, the 2,4'-dipyridyl derivative is preferentially produced (see Examples 1 and 2).

The nickel complex catalyst used in the coupling reaction is, for example, bis(triphenylphosphine) nickel (II) dihalides, such as $NiCl_2$ $(PPh_3)_2$, $NiBr_2$ $(PPh_3)_2$, $NiI_2$ $(PPh_3)_2$, $NiCl_2$ $[Ph_2P(CH_2)_2 PPh_2]$, $NiCl_2$ $[Ph_2P(CH_2)_3 PPh_2]$, or $Ni (PPh_3)_4$, $Ni(1,5-cyclooctadiene)_2$ (Ph indicates phenyl group), preferably $NiCl_2$ $(PPh_3)_2$, $NiBr_2$ $(PPh_3)_2$, $NiCl_2$ $[Ph_2P(CH_2)_2PPh_2]$, or $Ni (PPh_3)_4$, most preferably $NiCl_2$ $(PPh_3)_2$ or $NiBr_2$ $(PPh_3)_2$ is used in an amount of preferably 10 to 50 mol %, more preferably 30 mol %, based upon the 2-halopyridine derivative and 4-halopyridine.

When the catalyst is bivalent nickel, the reaction proceeds well in the copresence of zinc.

The zinc used in the reaction is used in an amount-of preferably 1 to 4 equivalents, more preferably 1.5 equivalents, of the 2-halopyridine derivative and 4-halopyridine. The alkyl group constituting the tetraalkylammonium halide, is preferably a lower alkyl group, more preferably a methyl group, ethyl group, n-propyl group, or n-butyl group, most preferably an ethyl group or n-butyl group. The halogen is iodine or bromine and is used in an amount of preferably 0.1 to 3 equivalents, more preferably 1 equivalent, of the 2-halopyridine derivative and 4-halopyridine.

When performing the coupling reaction of the 2-halopyridine derivative and 4-halopyridine, a nickel complex, zinc, and tetraalkylammonium halide are reacted in an organic solvent, for example, tetrahydrofuran, toluene, acetone, ethyl ether, dimethyl formamide, or their mixtures, preferably tetrahydrofuran, to obtain a catalyst solution, and then to this solution, the 2-halopyridine derivative or a salt thereof and 4-halopyridine or a salt thereof are added directly or as a mixture prepared in advance. The mixture thus obtained is comprised of the 2-halopyridine derivative or a salt thereof and 4-halopyridine or a salt thereof neutralized in an organic solvent. As the organic solvent, for example, acetone, tetrahydrofuran, ethyl ether, or dimethylformamide, preferably dimethylformamide, is used. The amine is preferably triethylamine.

The reaction of the 2-halopyridine derivative and 4-halopyridine is performed preferably at 0° C. to 70° C., more preferably 40° C. to 60° C., but if the temperature rises too high at the time of addition, the yield is decreased, and therefore the solution is appropriately cooled through the addition.

When using dimethylformamide as the reaction solution, the reaction is also carried out without using a tetraalkylammonium halide (see Examples 5 and 8).

Further, the concentration of the reaction mixture is preferably medium to low concentration since the presence of the catalyst as a solid in the reaction mixture makes its reaction at a high concentration difficult (see Examples 17 and 18).

The reaction mixture is poured into a dilute aqueous ammonia solution to terminate the reaction then an organic solvent is added, the insolubles are filtered out, and a separation operation performed to obtain an organic layer which is then condensed. In the reduced pressure distillation of the organic layer, separation from phosphine or other isomers is difficult. In the present invention, the following two separation methods may be used.

II. Method of Separation and Purification of 2,4'-Dipyridyl Derivative

1. By Column Chromatography (see Examples 1 to 9)

The above condensate is dissolved in an organic solvent and subjected to silica gel column chromatography, whereupon triphenylphosphine is eluted by hexane, 2,2'-dipyridyl derivative is eluted by hexane-ethyl acetate (4:1), the desired 2,4'-dipyridyl derivative is eluted by ethyl acetate, and 4,4'-dipyridyl is eluted after the 2,4'-dipyridyl derivative.

2. By Formation of Copper Salt (Examples 10 to 18)

When separating and purifying the 2,4'-dipyridyl derivative from the reaction mixture, the separation of the triphenylphosphine and dipyridyl derivative mixture is performed by transfer to an aqueous layer in the presence of an acid, preferably hydrochloric acid (gas or aqueous solution), then the aqueous layer is made basic and extracted with an organic solvent. The 2,4'-dipyridyl derivative is separated from the mixture of dipyridyl isomers contained in the extract by insolubilizing the 2,2'-dipyridyl derivative and 4,4'-dipyridyl by a dilute aqueous copper sulfate solution.

To make the copper salts formed other than that of the 2,4'-dipyridyl derivative selectively precipitate, the setting of the concentration of the copper sulfate is important. A range of 0.1M to 0.2M is desirable.

As the extraction solvent, any organic solvent can be used if it can be separated from water and is low in toxicity, but in general toluene, ethyl acetate, chloroform, tetrahydrofuran, or ethyl ether is preferred.

As mentioned above, a method of separation of a 2,4'-dipyridyl derivative from a reaction mixture by a cross coupling reaction using a 2-halopyridine derivative and 4-halopyridine as the starting materials and using a nickel complex catalyst is described, but the method of separation of the 2,4'-dipyridyl derivative of the present invention clearly can also be used for the separation of a 2,4'-dipyridyl derivative from a mixture of 2,21-dipyridyl derivative, 2,4'-dipyridyl derivative, and 4,4'-dipyridyl synthesized by any other method.

III. Method of Production of Benzoxazepine Derivatives

The present inventors conducted intensive studies on synthesis using affinity with a serotonergic receptor and the affinity with a dopamine $D_2$ receptor as activity indicators and found that the specific benzoxazepine derivatives and their salts having the formula (III) exhibit an anxiolytic activity confirmed by the anticonflict activity and that they have suppressive activity in cerebral infarction and other protective effect of the brain in ischemic brain diseases in a transient right middle cerebral artery occlusion (MCAO) model, and therefore, found that these compounds were useful as more effective pharmaceuticals with less side effects used for the treatment of anxiety neurosis, phobias, obsessive-compulsive disorders, schizophrenia, post-cardiac trauma stress disorders, depression disorders, psychosomatic disorders and other psychoneurotic disorders, eating disorders, menopausal disorders, infantile autism and other disorders, and also emesis or disorders involving the cerebral circulatory system accompanying cerebral infarction and cerebral hemorrhage (see specification of International Patent Publication WO/96/24594). They then found a useful method for the production of the same and completed the present invention.

Accordingly, another object of the present invention is to provide method of production of said benzoxazepine derivatives.

In accordance with the present invention, there is further provided a method of producing benzoxazepine derivatives having the formula (III):

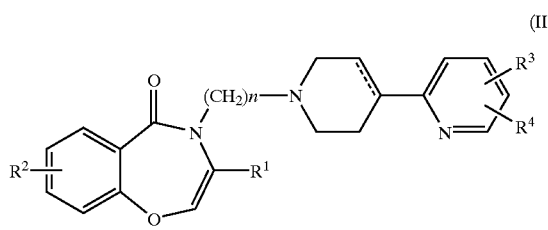

(III)

wherein n represents an integer of 2 to 5, $R^1$ represents a hydrogen atom, a halogen atom, $C_1$–$C_4$ lower alkyl group, $C_1$–$C_4$ lower alkoxyalkyl group, $C_1$–$C_4$ halogenoalkyl group, cyano group, or ester group, $R^2$ represents a hydrogen atom, a halogen atom, $C_1$–$C_4$ lower alkyl group, $C_1$–$C_4$ lower alkoxy group, or hydroxy group, $R^3$ and $R^4$ independently represent a hydrogen atom, halogen atom, or $C_1$–C4 lower alkyl group, and a dotted line indicates the presence or absence of a bond and its salts.

In accordance with the present invention, there is further provided a method of producing benzoxazepine derivatives having the formula (V):

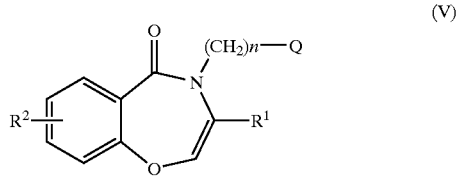

(V)

wherein n, $R^1$, and $R^2$ are as defined above and Q indicates a hydroxy group, alkoxy group, halogen, or leaving group capable of being easily exchanged with an amino group and its salts. This is useful as a method of production of an intermediate for synthesis of the benzoxazepine derivatives having the formula (III) and salts thereof.

In accordance with the present invention, further, there is provided a method of production of a benzoxazepine derivative having the formula (VI):

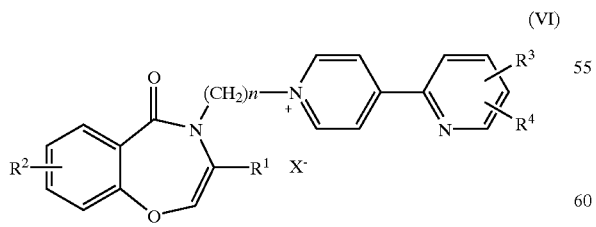

(VI)

wherein, n, $R^1$, $R^2$, $R^3$, and $R^4$ are as defined above and X represents a halogen atom and its salts. This is useful as a method of production of a synthetic intermediate of the benzoxazepine derivative having the formula (III) and its salts.

Furthermore, a more detailed explanation will now be given of the mode of working the invention in the method of production of the compound having the formula (III) according to the examples of the present invention, but of course the present invention is not limited to these examples.

In the compound of the formula (III), as preferable examples of the integer n in the formula, 3 to 5 may, be mentioned, in particular, 4 is preferable. As preferable examples of the group $R^1$ in the formula (III), a hydrogen atom, $C_1$–$C_3$ lower alkyl group, $C_1$–$C_3$ lower alkoxyalkyl group, $C_1$–$C_2$ halogenoalkyl group, chlorine atom, or nitrile group may be mentioned, but a hydrogen atom, methyl group, ethyl group, methoxymethyl group, chloromethyl group, or chlorine atom is particularly preferable. As preferable examples of the group $R^2$, a hydrogen atom, halogen atom, $C_1$–$C_2$ lower alkyl group, $C_1$–$C_2$ lower alkoxy group, or hydroxy group may be mentioned, but a hydrogen atom, fluorine atom, chlorine atom, methyl group, or methoxy group is particularly preferable.

The method of production of a compound having the formula (III) according to the present invention is, for example, the following method of production:

First, in the intermediate compound having the formula (V) according to the present invention, the preferable examples of the integer n in the formula are 3 to 5, more preferably 4. The preferable examples of the group $R^1$ in the formula are, a hydrogen atom, $C_1$–$C_3$ lower alkyl group, $C_1$–$C_3$ alkoxyalkyl group, $C_1$–$C_2$ halogenalkyl group, chlorine atom, and nitrile group, particularly preferably a hydrogen atom, methyl group, ethyl group, methoxymethyl group, chloromethyl group, or chlorine atom. The preferable examples of the group $R^2$ are, a hydrogen atom, halogen group, $C_1$–$C_2$ lower alkyl group, $C_1$–$C_2$ lower alkoxy group, and hydroxy group, particularly preferably a hydrogen atom, fluorine atom, chlorine atom, methyl group, or methoxy group. Further, the preferable examples of the leaving group easily exchangeable with a hydroxy group, alkoxy group, halogen, or amino group of the group Q in the formula are a tosyl group, mesyl group, chlorine atom, bromine atom, and iodine atom, particularly preferably a chlorine atom, bromine atom, or iodine atom.

The production method of a useful synthetic intermediate having the formula (V) may be, for example, comprised as follows. The production method of the compound having the formula (V) where, for example, $R^1$ and $R^2$ are hydrogen atoms and Q is a chlorine atom, that is, a compound having the formula (Va):

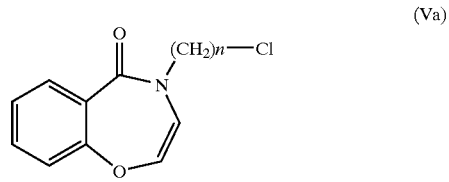

(Va)

wherein n is the same as defined above, is comprised of reacting the compound, obtained according to the method described in the reference of H. Hofmann et al. (Liebigs Ann. Chem., p. 917, 1990) or similar methods, having the formula (X):

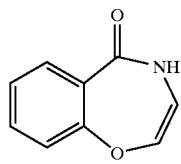

(X)

with, for example, bromochloroalkane, to obtain the useful synthetic intermediate, benzoxazepine derivative (Va).

Also in the production method of a compound having the formula (V), a production method of the compound having the formula (V) where, for example, $R^1$ is a methyl group, $R^2$ is a hydrogen atom, and Q is a chlorine atom, i.e., a compound having the formula (Vb):

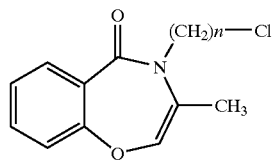

(Vb)

wherein n is the same as defined above, is comprised of reacting the compound, obtained according to the method described in the reference of J. Freedmann et al. (J. Heterocyclic Chem., vol. 27, p. 343, 1990) or similar methods; having the formula (XI):

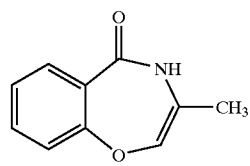

(XI)

with, for example, bromochloroalkane, to obtain the useful synthetic intermediate, benzoxazepine derivative (Vb).

Furthermore, in the production method of a compound having the formula (V), a production method of the compound (V) where, for example, $R^1$ is a halogen atom such as a chlorine atom, $R^2$ is a hydrogen atom, and Q is a chlorine atom, a compound having the formula (Vc):

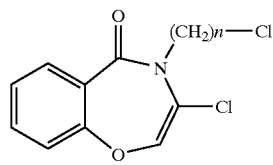

(Vc)

wherein n is the same as defined above, is comprised of reacting the compound, obtained according to the method described in the reference of A. Cattaneo et al. (Boll. Chim. Farm., vol. 102, p. 541, 1963) or similar methods, having the formula (XII):

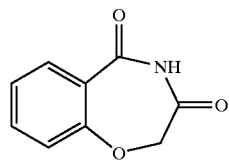

(XII)

with, for example, bromochloroalkane to obtain a compound having the formula (XIII):

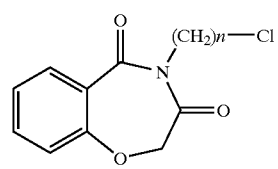

(XIII)

wherein n is the same as defined above, then, reacting with an acid chloride such as phosphorus oxychloride, thionyl chloride, while optionally adding an acid such as hydrochloric acid or a base such as N,N-diethylaniline, to obtain the useful synthetic intermediate, benzoxazepine derivative (Vc).

The production method of the benzoxazepine derivative (Vc) may further be comprised of the following separate method, as an alternative method. That is, the compound having the above general formula (XII) is reacted with an acid chloride such as phosphorus oxychloride, thionyl chloride, while optionally adding an acid such as hydrochloric acid or a base such as N,N-diethylaniline to convert the same to a compound having the formula (XIV):

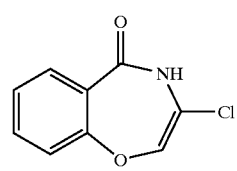

(XIV)

and reacting with, for example, bromochloroalkane.

In the production method of a compound having the formula (V), a production method of the compound (V) where, for example, where $R^1$ is a halomethyl group, for example, a chloromethyl group, $R^2$ is a hydrogen atom, and Q is a chlorine atom, a compound having the formula (Vd):

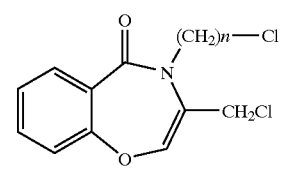

(Vd)

wherein n is the same-as defined above, is comprised of reacting the compound of the above, intermediate (Vb) with N-chlorosuccinimide, to obtain the useful synthetic intermediate, benzoxazepine derivative (Vd).

Further, in the production method of a compound having the formula (V), a production method of the compound (V) where, for example, where $R^1$ is a $C_1$–$C_4$ lower alkoxymethyl group, for example, a methoxymethyl group, $R^2$ is a hydrogen atom, and Q is a bromine atom, a compound having the formula (Ve):

(Ve)
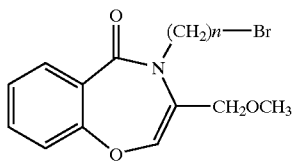

wherein n is the same as defined above, is comprised of reacting the compound of the above intermediate (XI) with N-chlorosuccinimide to convert the same to the compound (XV) having the following structure:

(XV)
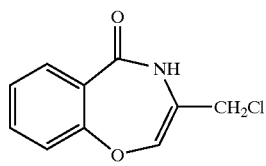

then using sodium methoxide to convert the same to a compound having the following structure (XVI):

(XVI)
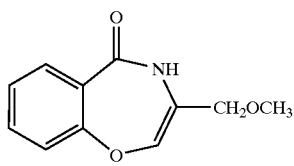

followed by reacting with dibromoalkane, to obtain the useful synthetic intermediate, benzoxazepine derivative (Ve).

In the production method of a compound having the formula (V), a production method of, for example, a compound having the formula (Vf):

(Vf)
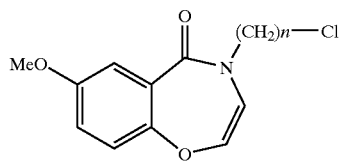

where n is the same as defined above, i.e., $R^1$ is a hydrogen atom, $R^2$ is an alkoxy group, for example, 7-methoxy group, and Q is a chlorine atom in the formula (V), is comprised of following the method described in the above reference of H. Hofmann et al. or similar methods to obtain the compound having the formula (XVII):

(XVII)
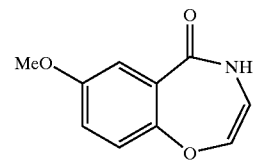

then following the same procedure for synthesizing a compound having-the above formula (Va).

In the production method of a compound having the formula (V), a production method of, for example, a compound having the formula (Vg):

(Vg)
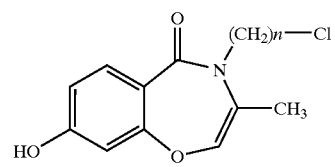

wherein n is the same as defined above, i.e., $R^1$ is an alkyl group, for example, a methyl group, $R^2$ is an 8-hydroxy group, and Q is a chlorine atom in the formula (V), is comprised of following the method described in the above reference of J. Freedmann et al. or similar methods to obtain the compound having the formula (XVIII):

(XVIII)
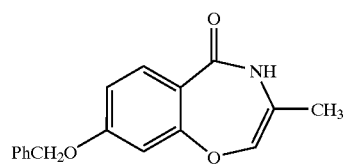

then following the same procedure as synthesizing the compound having the above formula (Vb) to obtain the compound having the formula (XIX):

(XIX)
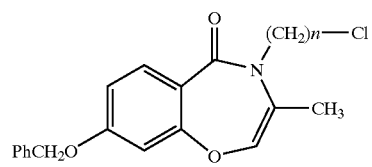

wherein n is the same as defined above, and then removing the benzyl group by a catalytic reduction.

In the production method of a compound having the formula (V), a production method of, for example, a compound having the formula (Vh):

(Vh)
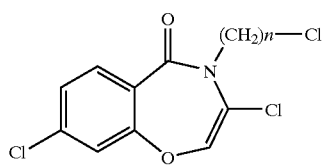

wherein n is the same as defined above, i.e., $R^1$ and Q are halogen atoms, for example, chlorine atoms, and $R^2$ is an 8-chloro group in the formula (V), is comprised of following the method described in the above reference of A. Cattaneo et al. or similar methods to obtain the compound having the formula (XX):

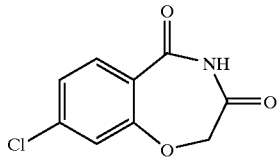

and following the same procedure as for synthesizing the compound having the above formula (Vc).

In the production method of the compound having the formula (V), a compound where, for example, $R^1$ is a nitrile group, $R^2$ is a hydrogen atom, and Q is a chlorine atom, that is, a compound having the formula (Vi):

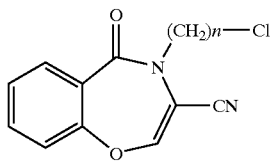

wherein n is the same as defined above, may comprise reacting trimethylsilyl nitrile to a compound having the above formula (XIII), if necessary, in the presence of zinc iodide or reacting trimethylsilyl nitrile to a compound having the above formula (Vc) in the presence of a palladium catalyst.

In the production method of the compound having the formula (V), a production method of, for example, a compound having the formula (Vj):

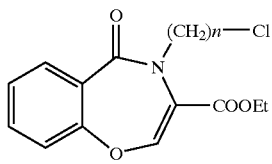

where n is the same as defined above, i.e., $R^1$ is an ester group, for example, an ethyl ester, $R^2$ is a hydrogen groups and Q is a chlorine group in the formula (V), is comprised of reacting ethanol to a compound having the above formula (Vi) in the presence of an acid catalyst.

1) Synthesis of Final Compound Having Formula (III)

The production method of the compound having the formula-(III) may be comprised of condensation reacting the benzoxazepine derivative having the formula (V) and an intermediate compound having the formula (XXI):

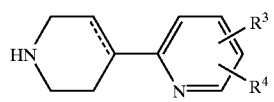

wherein $R^3$, $R^4$ and the dotted line are the same as defined above, by an ordinary method.

Here, the intermediate having the formula (V) may be synthesized by the same procedure as the synthesis of the compounds having the general formulas (Va) to (Vj) shown above, for example.

Further, the production method of a pyridine derivative (XXIa):

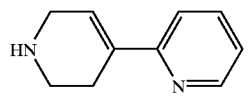

where, in general formula (XXI), $R^3$ and $R^4$ are hydrogen atoms and the dotted line indicates the presence of a bond may be comprised of following the method described in reference of H. Fischer et al. (J. Heterocyclic. Chem., vol. 17, p. 333, 1980) or similar methods to convert the known compound 2,4'-dipyridyl to a compound having the formula (XXII):

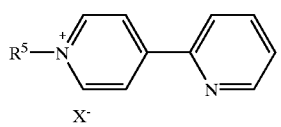

wherein $R^5$ is a $C_1$–$C_4$ lower alkyl group, benzyl group, or methoxybenzyl group and X is a halogen atom, then reducing it with sodium borohydride to obtain a compound having the formula (XXVIIIa):

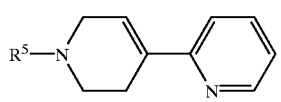

wherein $R^5$ is the same as defined above, then reacting the compound with ethyl chloroformate, phenyl chloroformate, 1-chloroethyl chloroformate, or 2-trimethylsilylethyl chloroformate etc. to obtain a compound of the general formula (XXIVa):

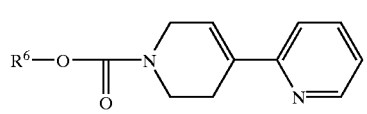

wherein $R^6$ is a $C_1$–$C_4$ lower alkyl group, 1-chloroethyl group, phenyl group, or 2-trimethylsilylethyl group.

The compound thus obtained is then decomposed with an alcohol such as methanol, ethanol, or hydrolyzed with an acid such as hydrochloric acid, acetic acid, sulfuric acid, hydrobromic acid, or decomposed with a fluoride such as tetrabutylammonium fluoride (TBAF) so as to obtain the useful synthetic intermediate pyridine derivative having the formula (XXIa).

Further, for example, the pyridine derivative (XXIb)

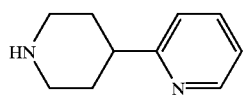
(XXIb)

where, in the general formula (XXI), for example, $R^3$ and $R^4$ are hydrogen atoms and the dotted line indicates the absence of a bond can be obtained by hydrogenattas the compound having the formula (XXIIIa) in the presence of a palladium/carbon catalyst and, optionally, by adding an acid-such as hydrochloric acid to obtain the compound having the formula (XXIIIb):

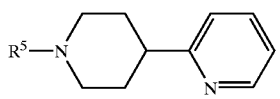
(XXIIIb)

wherein $R^5$ is the same as defined above, then reacting the compound with ethyl chloroformate, phenyl chloroformate, 1-chloroethyl chloroformate, 2-trimethylsilylethyl chloroformate, etc. to obtain the compound having the formula (XXIVb):

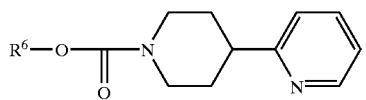
(XXIVb)

wherein $R^6$ is a $C_1$–$C_4$ lower alkyl group, 1-chloroethyl group, phenyl group, or 2-trimethylsilylethyl group.

The obtained compound (XXIVb) is then decomposed with an alcohol such as methanol, ethanol, or hydrolyzed with an acid such as hydrochloric acid, acetic acid, sulfuric acid, bromic acid, or decomposed with a fluoride such as tetrabutylammonium fluoride (TBAF) so as to obtain the useful synthetic intermediate pyridine derivative (XXIb).

The piperidylpyridine (XXIb) can be obtained by direct catalytic reduction of 1,2,3,6-tetrahydropyridyl pyridine having the formula (XXIa).

The production method of the final compound (III) comprises replacement condensation of a synthetic intermediate having the formula (XXI), for example, a synthetic intermediate pyridine derivative such as illustrated in the above (XXIa to XXIb), with the synthetic intermediate (V) such as illustrated in the above (Va to Vj) and optionally, using a catalyst such as a base (e.g., triethylamine or potassium carbonate) or sodium iodide.

2) Synthesis of Final Compound Having Formula (III) by Separate Method

The production method of the final compound (III) may be comprised of synthesis through the synthetic intermediate having the formula (VI):

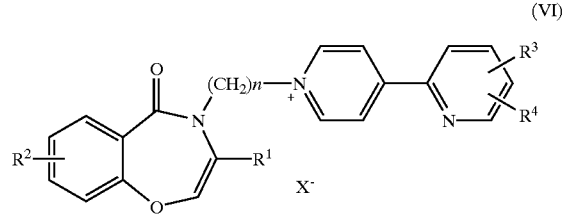
(VI)

where $R^1$, $R^2$, $R^3$, $R^4$, X, and n are the same as defined above.

Here, the production method of the synthetic intermediate having the formula (VI) may be carried out as follows: That is, a production method of a useful synthetic intermediate having the above formula (VI) by reacting a 2,4'-dipyridyl derivative having the above formula (II) to the compound having the formula (Vk), which corresponds to the compound having the above formula (V), where, for example, Q is a chlorine atom;

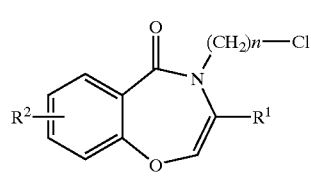
(Vk)

wherein $R^1$, $R^2$, and n are the same as defined above in the presence of sodium iodide.

It may also be comprised as a method of production of a final compound (III) by reacting sodium borohydride to the synthetic intermediate (VI) obtained.

Examples 19 to 27 show the production methods of the above benzoxazepine derivatives and the salts thereof.

The present invention will now be explained in further detail with reference to Examples, but, of course, the scope of the present invention is not limited to these Examples.

EXAMPLES

Example 1

Production Method of 2,4'-Dipyridyl Using bis (triphenylphosphine) Nickel (II) Dibromide as Nickel Complex (2-Chloropyridine:4-chloropyridine=4:1)

The following reaction was performed under an argon gas flow.

1.11 g (1.5 mmoles) of bis(triphenylphosphine) nickel (II) dibromide (made by Aldrich), 490 mg (7.5 mmoles) of zinc powder, and 1.28 g (5 mmoles) of tetraethylammonium iodide ($Et_4NI$) were suspended in 10 ml of anhydrous tetrahydrofuran (THF) and the resulting mixture was stirred at room temperature for 30 minutes. To the reaction mixture, a mixture obtained by stirring 380 µl (4 mmoles) of 2-chloropyridine, 150 mg (1 mmole) of 4-chloropyridine hydrochloride, and 140 µl (1 mmole) of triethylamine in 5 ml of dimethylformamide (DMF) for 1 hour was added, by a syringe.

After the reaction solution was stirred at 50° C. for 16 hours, the reaction mixture was poured into 50 ml of a 2N aqueous ammonia solution, 20 ml of ethyl acetate and 20 ml of toluene were added, and the insolubles were filtered out.

A separation operation was performed to obtain an organic layer and an aqueous layer which were extracted by 20 ml toluene-, combined, and washed by saturated saline. The organic layer obtained was concentrated under reduced pressure.

The residue was purified with silica gel chromatography (Wakogel C-200 (trademark) 10 g, 2 cm diameter×7 cm).

Triphenylphosphine was eluted with hexane, and 2,2'-dipyridyl was eluted with hexane-ethyl acetate (4:1). The desired 2,4'-dipyridyl was eluted with ethyl acetate.

The eluted fraction was concentrated to obtain 73 mg of 2,2'-dipyridyl (yield 23%, calculated from 2-chloropyridine) and 99 mg of 2,4'-dipyridyl (yield 63%, calculated by 4-chloropyridine).

Example 2

Production Method of 2,4'-Dipyridyl Using bis (Triphenylphosphine) Nickel (II) Dibromide as Nickel Complex (2-Chloropyridine:4-chloropyridine=3:2)

The method of Example 1 was repeated except that the amounts of the 2-chloropyridine, 4-chloropyridine hydrochloride, and triethylamine were changed to 285 μl (3 mmoles), 300 mg (2 mmoles), and 280 μl (2 mmoles), respectively, and the 4,4'-dipyridyl was eluted with ethyl acetate after the elution of 2,4'-dipyridyl to thereby obtain 45 mg of 2,2'-dipyridyl (yield 19%, calculated from 2-chloropyridyl), 193 mg of 2,4'-dipyridyl (yield 61%, calculated from 4-chloropyridine), and 57 mg of 4,4'-dipyridyl (yield 36%, calculated from 2-chloropyridine).

Example 3

Production Method of 2,4'-Dipyridyl Using bis (Triphenylphosphine) Nickel (II) Dichloride as Nickel Complex (2-Chloropyridine:4-chloropyridine=4:1)

The following reaction was performed under an argon gas flow.

981 mg (1.5 mmoles) of bis(triphenylphosphine) nickel (II) dichloride (made by Tokyo Kasei), 490 mg (7.5 mmoles) of zinc powder, and 1.28 g (5 mmoles) of tetraethylammonium iodide-were suspended in 10 ml of anhydrous tetrahydrofuran and the resulting mixture was stirred at room temperature for 30 minutes. To the reaction mixture a mixture obtained by stirring 379.2 μl (4 mmoles) of 2-chloropyridine, 150 mg (1 mmole) of 4-chloropyridine hydrochloride, and 139.2 μl 1 mmole) of triethylamine in 5 ml of dimethylformamide for 1 hour was added, by a syringe.

After the reaction solution was stirred at 50° C. for 16 hours, the reaction mixture was poured into 50 ml of a 2N aqueous ammonia solution, 20 ml of ethyl acetate and 20 ml of toluene were added, and the insolubles were filtered out. A separation operation was performed to obtain an organic layer and aqueous layer which were extracted with 20 ml toluene, combined, and washed with saturated saline. The organic layer obtained was concentrated under reduced pressure.

The residue was purified with silica gel chromatography (Wakogel C-200 (trademark) 10 g, 2 cm diameter×7 cm).

Triphenylphosphine was eluted with hexane, and 2,2'-dipyridyl was eluted with hexane-ethyl acetate (4:1). The desired 2,4'-dipyridyl was eluted with ethyl acetate.

The eluted fraction was concentrated to obtain 88 mg of 2,2'-dipyridyl (yield 28%, calculate from 2-chloropyridine) and 132 mg of 2,4'-dipyridyl (yield 84%, calculated from 4-chloropyridine).

Example 4

Production Method of 2,4'-Dipyridyl Using bis (Triphenylphosphine) Nickel (II) Dichloride as Nickel Complex (2-Chloropyridine:4-chloropyridine=1:1)

The method of Example 3 was repeated except that the amounts of the 2-chloropyridine, 4-chloropyridine hydrochloride, and triethylamine were changed to 237 μl (2.5 mmoles), 375 mg (2.5 mmoles), and 348 μl (2.5 mmoles) respectively and the 4,4'-dipyridyl was eluted after the elution of the 2,4'-dipyridyl to thereby obtain 72 mg of 2,2'-dipyridyl (yield 18%, calculated as 2.5 mmoles=100%), 198 mg of 2,4'-dipyridyl (yield 51%), and 57 mg of 4,4'-dipyridyl (yield 15%, calculated as 2.5 mmoles=100%).

The reaction conditions and results obtained in Examples 1 to 4 are shown in the following Table 1. In the Table, Ph represents a phenyl group.

TABLE 1

|  | Ex. 1 | Ex. 2 | Ex. 3 | Ex. 4 |
| --- | --- | --- | --- | --- |
| Preparation of catalyst |  |  |  |  |
| Nickel complex catalyst (30 mol %) | NiBr$_2$ (PPh$_3$)$_2$ 1.11 g | NiBr$_2$ (PPh$_3$)$_2$ 1.11 g | NiCl$_2$ (PPh$_3$)$_2$ 981 mg | NiCl$_2$ (PPh$_3$)$_2$ 981 mg |
| Zinc (1.5 equivalents) | 490 mg | 490 mg | 490 mg | 490 mg |
| Et$_4$NI (1 equivalent) | 1.28 g | 1.28 g | 1.28 g | 1.28 g |
| Solvent | THF | THF | THF | THF |
| Reaction time | 30 min. | 30 min. | 30 min. | 30 min. |
| Preparation of material |  |  |  |  |
| 2-Cl-pyridine | 4 mmol | 3 mmol | 4 mmol | 2.5 mmol |
| 4-Cl-pyridine.HCl | 1 mmol | 2 mmol | 1 mmol | 2.5 mmol |
| Triethylamine | 1 mmol | 2 mmol | 1 mmol | 2.5 mmol |
| Solvent | DMF | DMF | DMF | DMF |
| Reaction time | 1 hr | 1 hr | 1 hr | 1 hr |
| Reaction |  |  |  |  |
| Reaction temperature | 50° C. | 50° C. | 50° C. | 50° C. |
| Reaction time | 16 hr | 16 hr | 16 hr | 16 hr |
| Results |  |  |  |  |
| 2,2'-dipyridyl Yield | 73 mg | 45 mg | 88 mg | 72 mg |
| % Yield | (23%) | (19%) | (28%) | (18%) |
| 2,4'-dipyridyl Yield | 99 mg | 193 mg | 132 mg | 198 mg |
| % yield | 63% | 61% | 84% | 51% |
| 4,4'-dipyridyl Yield | — | 57 mg | — | 57 mg |
| % yield | 0% | (36%) | 0% | 15% |

The percent yield was the yield from 2-chloropyridine or 4-chloropyridine. The yield from 2-chloropyridine is shown in parentheses. In Example 4, the ratio of starting materials was 1:1, and therefore, the yield was made 100%=2.5 mmoles.

The next Examples 5 to 7 explain the method of addition of the reaction catalyst and the starting materials.

Example 5

The method of Example 4 was repeated except that the catalyst preparation reaction solvent was changed to dimethylformamide from tetrahydrofuran and tetraethylammonium iodide was not added, whereby 43 mg. (yield 11%) of 2,2'-dipyridyl, 161 mg (yield 41%) of 2,4'-dipyridyl, and 81 mg (yield 21%) of 4,4'-dipyridyl were obtained.

Example 6

The method of Example 4 was repeated except that as the catalyst preparation reaction solvent, 10 ml of tetrahydrofuran and 5 ml of dimethylformamide were used instead of 10 ml of tetrahydrofuran and the addition of 4-chloropyridine was carried out 4-chloropyridine hydrochloride in dimethylformamide by triethylamine, by directly adding 4-chloropyridine hydrochloride to the catalyst reaction solution, followed by adding triethylamine, instead of the addition thereof by neutralizing 4-chloropyridine hydrochloride with triethylamine in the dimethylformamide, whereby 28 mg (yield 7%) of 2,2'-dipyridyl, 163 mg (yield 42%) of 2,4'-dipyridyl, and 103 mg (yield 26%) of 4,4'-dipyridyl were obtained.

Example 7

The method of Example 4 was repeated except that acetone was used as the catalyst reaction solvent, whereby 65 mg (yield 17%) of 2,2'-dipyridyl, 1.13 mg (yield 29%) of 2,4'-dipyridyl, and 24 mg (yield 6%) of 4,4'-dipyridyl.

The reaction conditions and the results obtained in Examples 5 to 7 are shown in Table 2.

TABLE 2

| | Ex. 5 | Ex. 6 | Ex. 7 |
|---|---|---|---|
| Preparation of catalyst | | | |
| Nickel complex catalyst (30 mol %) | NiCl$_2$(PPh$_3$)$_2$ 981 mg | NiCl$_2$(PPh$_3$)$_2$ 981 mg | NiCl$_2$(PPh$_3$)$_2$ 981 mg |
| Zinc | 490 mg | 490 mg | 490 mg |
| Et$_4$NI | — | 1.28 g | 1.28 g |
| Solvent | DMF | THF + DMF 10 ml + 5 ml) | Acetone |
| Reaction time | 30 min. | 30 min. | 30 min. |
| Preparation of material | | | |
| 2-Cl-pyridine | 2.5 mmol | 2.5 mmol | 2.5 mmol |
| 4-Cl-pyridine HCl | 2.5 mmol | 2.5 mmol | 2.5 mmol |
| Triethylamine | 2.5 mmol | 2.5 mmol | 2.5 mmol |
| Solvent | DMF | Direct addition | Acetone |
| Reaction time | 1 hr | | 1 hr |
| Reaction | | | |
| Reaction temperature | 50° C. | 50° C. | 50° C. |
| Reaction time | 16 hr | 16 hr | 16 hr |
| Results | | | |
| 2,2'-dipyridyl Yield | 43 mg | 28 mg | 65 mg |
| % Yield | 11% | 7% | 17% |
| 2,4'-dipyridyl Yield | 161 mg | 163 mg | 113 mg |
| % yield | 41% | 42% | 29% |
| 4,4'-dipyridyl Yield | 81 mg | 103 mg | 24 mg |
| % yield | 21% | 26% | 6% |

The next Examples 8 to 9 explain the equivalent amounts of the catalyst.

Example 8

The method of Example 4 was repeated except that the catalyst preparation reaction solvent was changed to dimethylformamide, the amount of the nickel complex catalyst was changed 10 mol %, 327 mg (0.5 mmole), the amount of zinc was changed to 1.2 equivalents, 196 mg (3 mmoles), and tetraethylammonium iodide was not used, whereby 50 mg (yield 13%) of 2,2'-dipyridyl, 94 mg (yield 24%) of 2,4'-dipyridyl, and 70 mg (yield 18%) of 4,4'-dipyridyl were obtained.

Example 9

The method of Example 4 was repeated except that the amount of the nickel complex catalyst was changed to 10 mol %, 327 mg (0.5 mmole) and 427 mg (0.33 mole) of tetraethylammonium iodide was used, whereby 79 mg (yield 20%) of 2,2'-dipyridyl, 129 mg (yield 33%) of 2,4'-dipyridyl, and 103 mg (yield 26%) of 4,4'-dipyridyl were obtained.

The reaction conditions and the results obtained in Examples 8 and 9 are shown in Table 3.

TABLE 3

| | Ex. 8 | Ex. 9 |
|---|---|---|
| Preparation of catalyst | | |
| Nickel complex catalyst (10 mol %) | NiCl$_2$(PPh$_3$)$_2$ 327 mg | NiCl$_2$(PPh$_3$)$_2$ 327 mg |
| Zinc | 157 mg | 490 mg |
| Et$_4$NI | — | 427 mg |
| Solvent | DMF | THF |
| Reaction time | 30 min. | 30 min. |
| Preparation of material | | |
| 2-Cl-pyridine | 2.5 mmol | 2.5 mmol |
| 4-Cl-pyridine HCl | 2.5 mmol | 2.5 mmol |
| Triethylamine | 2.5 mmol | 2.5 mmol |
| Solvent | DMF | THF |
| Reaction time | 1 hr | 1 hr |
| Reaction | | |
| Reaction temperature | 50° C. | 50° C. |
| Reaction time | 16 hr | 16 hr |
| Results | | |
| 2,2'-dipyridyl Yield | 50 mg | 79 mg* |
| % Yield | 13% | 20%* |
| 2,4'-dipyridyl Yield | 94 mg | 129 mg |
| % yield | 24% | 33% |
| 4,4'-dipyridyl Yield | 70 mg | 103 mg |
| % yield | 18% | 26% |

*The impurities are contained.

Example 10

Separation Method of 2,4'-Dipyridyl by Formation of Copper Salts

The following reaction was performed under an argon gas flow.

19.6 g (30 mmoles) of bis(triphenylphosphine) nickel (II) dichloride (made by Tokyo Kasei), 9.8 g (150 mmoles) of zinc powder, and 25.7 g (100 mmoles) of tetraethylammonium iodide were suspended in 200 ml of anhydrous tetrahydrofuran (THF) and the resulting mixture was stirred at room temperature for 30 minutes. To the reaction mixture, a mixture obtained by stirring 4.73 ml (50 mmoles) of 2-chloropyridine, 7.5 g (50 mmole) of 4-chloropyridine hydrochloride, and 7.0 ml (50 mmole) of triethylamine in 100 ml of dimethylformamide for 1 hour was added, by a cannula.

The reaction solution was poured into 1 liter of a 2N aqueous ammonia solution, 200 ml of toluene was added, and the insolubles were filtered out by Celite. A separation operation was performed to obtain an organic layer and an aqueous layer which were extracted with 200 ml toluene, combined, and washed with saturated saline. The organic layer obtained was concentrated under reduced pressure.

The concentrate was dissolved in 100 ml of toluene and passed through hydrochloric acid gas to insolubilize the dipyridyls as a HCl-salts. The mixture of HCl-salts of the dipyridyl isomers was obtained by filtration to thereby separate the triphenylphosphine.

The above salts were dissolved in a mixture of 100 ml of toluene and 100 ml of water. The mixture was adjusted to an alkaline state with ammonia water, then was extracted 2 times by 100 ml of toluene. The combined organic layer was concentrated under reduced pressure to obtain a mixture of dipyridyl isomers.

The above dipyridyl isomer mixture was dissolved in 100 ml of toluene, then 200 ml of a 0.25M aqueous solution of copper sulfate was added and the mixture stirred to produce insolubles. The insolubles were filtered out using Celite, the toluene layer was washed with saturated saline, and the organic layer obtained was concentrated under reduced pressure to thereby obtain 656 mg (yield 8.4%) of 2,4'-dipyridyl in a substantially pure form.

The aqueous layer was adjusted to a pH of 9 with concentrated ammonia water, then was extracted two times with 100 ml of toluene. The organic layer was washed with saturated saline and concentrated under reduced pressure to obtain 1.77 g (yield 22.6%) of 2,4'-dipyridyl. The presence of a minute amount of 4,4'-dipyridyl was observed in this product. The total yield of the 2,4'-dipyridyl-by a 50 mmole scale was 31%.

Example 11

Separation Method of 2,4'-Diyridyl

The following reaction was performed under an argon gas flow.

981 mg (1.5 mmoles) of bis(triphenylphosphine) nickel (II) dichloride (made by Tokyo Kasei), 490 mg (7.5 mmoles) of zinc powder, and 1.28 g (5 mmoles) of tetraethylammonium iodide were suspended in 10 ml of anhydrous THF and the resulting mixture was stirred at room temperature for 30 minutes. To the reaction mixture, a mixture obtained by stirring 237 µl (2.5 mmoles) of 2-chloropyridine, 375 mg (2.5 mmole) of 4-chloropyridine hydrochloride, and 348 µl (2.5 mmoles) of triethylamine in 5 ml of DMF for 1 hour was added by a syringe.

The reaction solution was stirred at 50° C. for 16 hours, then the reaction mixture was poured into 50 ml of a 2N aqueous ammonia solution, 20 ml of toluene was added, and the insolubles were filtered out. A separation operation was performed to obtain an organic layer and aqueous layer which were extracted by 20 ml toluene, combined, and washed with saturated saline. The organic layer obtained was extracted with 20 ml of 1N hydrochloric acid. 20 ml of a 2N aqueous ammonia solution was added to this aqueous hydrochloric acid acidic solution, this was extracted two times by 20 ml of toluene, and the organic layer was washed with saturated saline and concentrated under reduced pressure to thereby obtain 311 mg of a dipyridyl isomer mixture.

This dipyridyl isomer mixture was dissolved in 10 ml of toluene, 20 ml of a 0.1M aqueous copper sulfate solution was added, and the resultant mixture was stirred, whereby insolubles were produced. The insolubles were filtered out using Celite, the toluene layer was washed with saturated saline, and the organic layer obtained was concentrated under reduced pressure, to thereby obtain 96.6 mg (yield 24.7%) of 2,4'-dipyridyl in a substantially pure form.

The aqueous layer was adjusted to a pH 9 with ammonia water, then extracted two times by 10 ml of toluene. The organic layer was washed with saturated saline and concentrated under reduced pressure, whereby a further 60.3 mg (yield 15.4%) of 2,4'-dipyridyl was obtained. The presence of a minute amount of 4,4'-dipyridyl was observed in this product. The total yield of the 2,4'-dipyridyl of the reaction was 40%.

Example 12

The following reaction was performed under an argon gas flow.

981 mg (1.5 mmoles) of bis(triphenylphosphine) nickel (II) dichloride (made by Tokyo Kasei), 490 mg (7.5 mmoles) of zinc powder, and 1.28 g (5 mmoles) of tetraethylammonium iodide were suspended in 10 ml of anhydrous toluene and the mixture was stirred at room temperature for 30 minutes. To the reaction mixture, a mixture obtained by stirring 237 41 (2.5 mmoles) of 2-chloropyridine, 375 mg (2.5 mmoles) of-4-chloropyridine hydrochloride, and 348 µl (2.5 mmoles) of triethylamine in 5 ml of DMF for 1 hour was added by a syringe.

Heat generation was observed in the reaction solution at this time and the temperature rose to close to 50° C. The reaction solution was stirred at 50° C. for 16 hours, then the reaction mixture was poured into 50 ml of a 2N aqueous ammonia solution, 20 ml of toluene was added, and the insolubles were filtered out. A separation operation was performed to obtain an organic layer and aqueous layer which were extracted by 20 ml toluene, combined, and washed with saturated saline. The organic layer obtained was extracted with 20 ml of 1N hydrochloric acid. 20 ml of a 2N aqueous-ammonia solution was added to an acidic solution, this was extracted two times with 20 ml of toluene, and the organic layer was washed with saturated saline and concentrated-under reduced pressure, whereby 376 mg of a dipyridyl isomer mixture was obtained.

This dipyridyl isomer mixture was dissolved in 10 ml of toluene, 20 ml of a 0.1M aqueous copper sulfate solution was added, and the result stirred, whereby insolubles, were produced. The insolubles were filtered out using Celite, the toluene layer was washed with saturated saline, and the organic layer obtained was condensed under reduced pressure, to thereby obtain 41.5 mg (yield 10.6%) of 2,4'-dipyridyl in a substantially pure form.

The aqueous layer was adjusted to a pH 9 with ammonia water, then extracted two times with 10 ml of toluene. The organic layer was washed with saturated saline and concentrated under reduced pressure, whereby a further 48.5 mg (yield 12.4%) of 2,4'-dipyridyl was obtained. The presence of a minute amount of 4,4'-dipyridyl was observed in this product. The total yield of the 2,41-dipyridyl of the reaction was 23%.

Example 13

The method used in Example 12 was carried out by ice cooling the reaction solution at the time when the 2-chloropyridine and 4-chloropyridine were added and by carrying out the reaction at room temperature, without heating.

The separation of the 2,4'-dipyridyl with copper sulfate was simplified by the following method.

This dipyridyl isomer mixture was dissolved in 10 ml of toluene, 20 ml of a 0.1M aqueous copper sulfate solution was added, and the resultant mixture was stirred, whereby insolubles were formed. The insolubles were filtered out using Celite. The toluene-aqueous copper sulfate solution was adjusted to a pH 9 with ammonia water, then extracted two times with 10 ml of toluene. The organic layer was washed with saturated saline and concentrated under reduced pressure, whereby a further 122 mg (yield 31%) of 2,4'-dipyridyl was obtained. The presence of a minute amount of 4,4'-dipyridyl was observed in this product.

The reaction conditions and results of separation of Examples 11 to 13 are shown in Table 4.

TABLE 4

| | Ex. 11 | Ex. 12 | Ex. 13 |
|---|---|---|---|
| Preparation of catalyst | | | |
| Nickel complex catalyst (30 mol%) | $NiCl_2(PPh_3)_2$ 981 mg | $NiCl_2(PPh_3)_2$ 981 mg | $NiCl_2(PPh_3)_2$ 981 mg |
| Zinc | 490 mg | 490 mg | 490 mg |
| $Et_4NI$ | 1.28 g | 1.28 g | 1.28 g |
| Solvent | THF | Toluene | Toluene |
| Reaction time | 30 min. | 30 min. | 30 min. |
| Preparation of material | | | |
| 2-Cl-pyridine | 2.5 mmol | 2.5 mmol | 2.5 mmol |
| 4-Cl-pyridine HCl | 2.5 mmol | 2.5 mmol | 2.5 mmol |
| Triethylamine | 2.5 mmol | 2.5 mmol | 2.5 mmol |
| Solvent | DMF | DMF | DMF |
| Reaction time | 1 hr | 1 hr | 1 hr |
| Reaction | | | |
| Reaction temperature | 50° C. | 50° C. | addition at 0° C. and, room temperature reaction |
| Reaction time | 16 hr | 16 hr | 16 hr |
| Results | | | |
| 2,2'-dipyridyl Yield | — | — | — |
| % Yield | — | — | — |
| 2,4'-dipyridyl Yield | 167 mg | 90 mg | 122 mg |
| % yield | 40% | 23% | 31% |
| 4,4'-dipyridyl Yield | — | — | — |
| % yield | — | — | — |

The following Examples 14 to 16 explain the types and equivalents of the quaternary ammonium salts and the equivalents of the catalysts.

Example 14

Example 11 was repeated except that the amount of the nickel complex catalyst was changed to 10 mol %, 327 mg (0.5 mmols). The total yield of 2,4'-dipyridyl was 98 mg (total yield 25%).

Example 15

Example 11 was repeated except that the amount of the tetraethylammonium iodide was changed to 30 mol %, 384 mg. The total yield of 2,4'-dipyridyl was 121 mg (total yield 31%).

Example 16

Example 11 was repeated except that 1.05 g (100 mol %) of tetraethylammonium bromide ($Et_4NBr$) was used, instead of tetraethylammonium iodide. The total yield of 2,4'-dipyridyl was 135 mg (total yield 35%).

The reaction-conditions and results of separation of Examples 14 to 16 are shown in Table 5.

TABLE 5

| | Ex. 14 | Ex. 15 | Ex. 16 |
|---|---|---|---|
| Preparation of catalyst | | | |
| Nickel complex catalyst (10 or 30 mol %) | $NiCl_2(PPh_3)_2$ 327 mg | $NiCl_2(PPh_3)_2$ 981 mg | $NiCl_2(PPh_3)_2$ 981 mg |
| Zinc | 490 mg | 490 mg | 490 mg |
| $Et_4NI$ | 1.28 g | 384 mg (30 mol %) | 1.05 g ($Et_4NBr$) |
| Solvent | THF | THF | THF |
| Reaction time | 30 min. | 30 min. | 30 min. |
| Preparation of material | | | |
| 2-Cl-pyridine | 2.5 mmol | 2.5 mmol | 2.5 mmol |
| 4-Cl-pyridine HCl | 2.5 mmol | 2.5 mmol | 2.5 mmol |
| Triethylamine | 2.5 mmol | 2.5 mmol | 2.5 mmol |
| Solvent | DMF | DMF | DMF |
| Reaction time | 1 hr | 1 hr | 1 hr |
| Reaction | | | |
| Reaction temperature | 50° C. | 50° C. | 50° C. |
| Reaction time | 16 hr | 16 hr | 16 hr |
| Results | | | |
| 2,2'-dipyridyl Yield | — | — | — |
| % Yield | — | — | — |
| 2,4'-dipyridyl Yield | 98 mg | 121 mg | 135 mg |
| % yield | 25% | 31% | 35% |
| 4,4'-dipyridyl Yield | — | — | — |
| % yield | — | — | — |

The following Examples 17 to 18 explain the reaction and the extraction concentration.

Example 17

(Reaction solution concentration: two times, extract concentration: ½)

The reaction was carried out under an argon gas flow. 1.96 g (3 mmoles) of bis(triphenylphosphine) nickel (II) dichloride (made by Tokyo Kasei), 940 mg (15 mmoles) of zinc powder, and 2.1 g (10 mmoles) of tetraethylammonium bromide were suspended in 10 ml of anhydrous THF and the mixture stirred at room temperature for 30 minutes. To the reaction mixture, a mixture obtained by stirring 474 μl (5 mmoles) of 2-chloropyridine, 750 mg (5 mmole) of 4-chloropyridine hydrochloride, and 696 μl (5 mmole) of triethylamine in 5 ml of DMF for 1 hour was added, by a syringe.

After the reaction solution was stirred at 50° C. for 16 hours, the reaction mixture was poured into 50 ml of a 4N aqueous ammonia solution, 20 ml of toluene was added, and the insolubles were filtered out. A separation operation was performed to obtain an organic layer and aqueous layer which were extracted with 20 ml toluene, combined, and washed with saturated saline. The organic layer obtained was extracted with 20 ml of 2N hydrochloric acid. 20 ml of a 4N aqueous ammonia solution was added to this aqueous hydrochloric acid acidic solution, this was extracted two times with 20 ml of toluene, and the organic layer was washed with saturated saline and concentrated under reduced pressure to thereby obtain 500 mg of a dipyridyl isomer mixture.

This dipyridyl isomer mixture was dissolved in 10 ml of toluene, 20 ml of a 0.2M aqueous copper sulfate solution was-added thereto, and the resultant mixture was stirred, whereby insolubles were formed. The insolubles were filtered out using Celite. The toluene-aqueous copper sulfate solution was adjusted to a pH 9 with ammonia water, then extracted two times with 10 ml of toluene. The organic layer was washed with saturated saline and concentrated under reduced pressure, whereby 231 mg (yield 30%) of 2,4'-dipyridyl was obtained. The presence of a minute amount of 4,4'-dipyridyl was observed in this product.

Example 18

(Reaction solution concentration: two times, extract concentration: ⅕)

The following reaction was performed in an argon gas flow.

4.9 g (7.5 mmoles) of bis(triphenylphosphine) nickel (II) dichloride (made by Tokyo Kasei), 2.35 g (37.5 mmoles) of zinc powder, and 5.2 g (25 mmoles) of tetraethylammonium bromide were suspended in 25 ml of anhydrous THF and the mixture was stirred at room temperature for 30 minutes. To the reaction mixture, a mixture obtained by stirring 1.19 ml (12.5 mmoles) of 2-chloropyridine, 1.88 g (12.5 mmoles) of 4-chloropyridine hydrochloride, and 1.74 ml (12.5 mmoles) of triethylamine in 12.5 ml of DMF for 1 hour was added by a syringe.

The reaction solution was stirred at 50° C. for 16 hours, then the reaction mixture was poured into 50 ml of a 10N aqueous ammonia solution, 30 ml of toluene was added, and the insolubles were filtered out. A separation operation was performed to obtain an organic layer and an aqueous layer which were extracted with 20 ml toluene, combined, and washed with saturated saline. The organic layer obtained was extracted with 20 ml of 2N hydrochloric acid. 20 ml of a 4N aqueous ammonia solution was added to this acidic solution, this mixture was extracted two times with 20 ml of toluene, and the organic layer was washed with saturated saline and concentrated under reduced pressure to thereby obtain 1.47 g of a dipyridyl isomer mixture.

This dipyridyl isomer mixture was dissolved in 10 ml of toluene, 20 ml of a 0.5M aqueous copper sulfate solution was added, and the resultant mixture was stirred, whereby insolubles were formed. The insolubles were filtered out using Celite. The toluene-aqueous copper sulfate solution was adjusted to a pH 9 with ammonia water, then extracted two times by 10 ml of toluene. The organic layer was washed with saturated saline and concentrated under reduced pressure, whereby 224 mg (yield 11%) of 2,4'-dipyridyl was obtained. The presence of a minute amount of 4,4'-dipyridyl was observed in this product. The insoublized copper salts obtained by filtration were adjusted to a pH 9 with ammonia water, then extracted 2 times with toluene. The organic layer was washed with saturated saline and then concentrated under reduced pressure, whereby 439 mg of a dipyridyl isomer mixture (including about one-third 2,4'-dipyridyl) was obtained.

The reaction conditions and results of separation of Examples 17 and 18 are shown in Table 6.

TABLE 6

|  | Ex. 17 | Ex. 18 |
| --- | --- | --- |
| Preparation of catalyst |  |  |
| Nickel complex catalyst (30 mol %) | NiCl$_2$(PPh$_3$)$_2$ 1.96 g | NiCl$_2$(PPh$_3$)$_2$ 4.9 g |
| Zinc | 940 mg | 2.35 mg |
| Et$_4$NI | 2.1 g | 5.2 g |
| Solvent (concentration: double) | THF (10 ml) | THF (25 ml) |
| Reaction time | 30 min. | 30 min. |
| Preparation of material |  |  |
| 2-Cl-pyridine | 2.5 mmol | 2.5 mmol |
| 4-Cl-pyridine HCl | 2.5 mmol | 2.5 mmol |
| Triethylamine | 2.5 mmol | 2.5 mmol |
| Solvent | DMF | THF |

TABLE 6-continued

|  | Ex. 17 | Ex. 18 |
| --- | --- | --- |
| Reaction time Reaction | 1 hr | 1 hr |
| Reaction temperature | 50° C. | 50° C. |
| Reaction time | 16 hr | 16 hr |
| Separation operation |  |  |
| Quenching of reaction solution | 4N NH$_3$ 50 ml | 10N NH$_3$ 50 ml |
| Hydrochloric acid | 2N 20 ml | 2N 20 ml |
| Ammonia water | 4N NH$_3$ 20 ml | 4N NH$_3$ 20 ml |
| Aqueous copper sulfate solution | 0.2N 20 ml | 0.5N 20 ml |
| Results |  |  |
| 2,2'-dipyridyl Yield | 231 mg | 224 mg |
| % yield | 30% | 11% |

Example 19

Synthesis of 3-Chloro-4-(4-chlorobutyl)-4,5-dihydro-1,4-benzoxazetin-5-one 5.0 g of 2,3,4,5-tetrahydro-1,4-benzoxazepine-3,5-dione was dissolved in 100 ml of acetone, 7.8 g (2 equivalents) of potassium carbonate and 6.5 ml (2 equivalents) of 1-bromo-4-chlorobutane were added, and the mixture heated and refluxed for 8 hours. The resultant mixture was allowed to cool, then filtered. The filtrate was concentrated and the residue obtained was dissolved in 50 ml of phosphorus oxychloride. Further, 20 ml of 4N hydrochloride dioxane-solution was added and the mixture stirred at 100° C. for 25 hours. The phosphorus oxychloride was distilled off and a 10% aqueous sodium hydroxide solution added under ice cooling. The mixture was extracted with methylene chloride, then was washed with a saturated aqueous solution of potassium bicarbonate and saturated saline and dried over anhydrous magnesium sulfate. The solvent was distilled off and the crude product obtained was purified by silica gel column chromatograph (hexane:ethyl acetate=6:1) to obtain 4.4 g of the above-identified compound (yield 45%).

Example 20

Synthesis of 3-Chloro-4,5-dihydro-4-(4-(4-(2-pyridyl)pyridinio-1-yl)butyl)-1,4-benzoxazepin-5-one Chloride 200 mg of the compound of Example 19 was dissolved in 2 ml of acetone, 21 mg (2 equivalents) of sodium iodide and 120 mg (1.1 equivalents) of 2,4'-dipyridyl were added, and the mixture heated and refluxed for 30 minutes. The resultant mixture was allowed to cool, then the precipitated crystals were obtained by filtration and recrystallization performed with a mixed solution of methanol, acetone, and ether to obtain 298 mg (yield 96%) of the above-identified compound.

Example 21

Synthesis of 3-Chloro-4,5-Dihydro-4-(4-(4-(2-pyridyl)piperidin-1-yl)butyl)-1,4-benzoxazepin-5-one 550 mg of the compound of Example 19 was dissolved in 10 ml of DMF, 210 mg (1.2 equivalents) of 4-(2-pyridyl) piperidine, 390 mg (2 equivalents) of sodium iodide and 0.36 ml (2 equivalents) of triethylamine were added, and the resultant mixture was stirred at 90° C. for 17 hours. The resultant mixture was allowed to cool, then water was added and the resultant mixture extracted two times with ethyl acetate. The entire organic layer was washed with a saturated aqueous solution of potassium bicarbonate and saturated saline and dried over anhydrous magnesium sulfate. The solvent was distilled off and the crude product obtained was purified by silica gel column chromatograph (methylene chloride:methanol=30:1) to obtain 450 mg of the above-identified compound (yield 85%). Note that a fumarate can be obtained by converting a fumarate by an ordinary method, then recrystallizing from acetone.

Example 22

Synthesis of 3-Chloro-4,5-Dihydro-4-(4-(4-(2-pyridyl)-1,2,3,6-tetrahydropyridin-1-yl)butyl)-1,4-benzoxazepin-5-one 487 mg of the compound of Example 19 was dissolved in 10 ml of DMF, 180 mg (1.2 equivalents) of 4-(2-pyridyl)-1,2,3,6-tetrahydropyridine, 336 mg (2 equivalents) of sodium iodide, and 0.31 ml (2 equivalents) of triethylamine were added, and the resultant mixture was stirred at 90° C. for 20 hours. The resultant mixture was processed and purified in the same way as Example 21 to obtain 290 mg of the above-identified compound (yield 63%). Note that a hydrochloride can be obtained by converting to a hydrochloride by an ordinary method, then recrystallizing from a mixed solvent of methanol and acetone.

Example 23

Synthesis of 4-(4-Bromobutyl)-4,5-dihydro-3-methyl-1,4-benzoxazenin-5-one 2.0 g of 3-methyl-4,5-dihydro-1,4-benzoxazepin-5-one was dissolved in 120 ml of dimethyllormamide, then 548 mg (1.2 equivalents) of 60% sodium hydride was added under ice cooling. This was stirred at room temperature for 1 hour, then 4.1 ml (3 equivalents) of 1,4-dibromobutane was added and the mixture was stirred for 3 hours. Ice water was added to the reaction solution and extraction was performed with ethyl acetate. The ethyl acetate extract was washed with saline, then dried over anhydrous magnesium sulfate. The solvent was distilled off and the resultant crude product was purified by silica gel column chromatography (hexane:ethyl acetate=4:1) to obtain 3.0 g of the above-identified compound (yield 84%).

Example 24

Synthesis of 4,5-Dihydro-3-methyl-4-(4-(4-(2-pyridyl)-1,2,3,6-tetrahydropyridin-1-yl)butyl)-1,4-benzoxazepin-5-one 230 mg of the compound of Example 23 was dissolved in 8 ml of dioxane, 100 mg (1.2 equivalents) of 4-(2-pyridyl)-1,2,3,6-tetrahydropyridine and 0.13 ml (1.5 equivalents) of triethylamine were added, and the resultant mixture was stirred at 80° C. for 10 hours. The resultant mixture was purified in the same way as in Example 21 to obtain 210 mg of the above-identified compound (yield 88%). Note that a fumarate can be obtained by converting to a fumarate by an ordinary method, then recrystallizing from a mixed solvent of acetone and ether.

Example 25

Synthesis of 4-(4-Chlorobutyl)-3,8-dichloro-4 5-dihydro-1,4-benzoxazepin-5-one 918 mg of 8-chloro-2,3,4,5-tetrahydro-1,4-benzoxazepine-3,5-dione was dissolved in 20 ml of acetone, 1.2 g (2 equivalents) of potassium carbonate and 819 mg (1.1 equivalents) of 1-bromo-4-chlorobutane were added, and the mixture heated and refluxed for 7 hours. The resultant mixture was allowed to cool, then filtered. The filtrate was condensed and the residue obtained was dissolved in 2 ml of phosphorus oxychloride. Further, 1.4 ml (2 equivalents) of N,N-diethylaniline was added and the mixture was stirred at 90° C. for 12 hours. The phosphorus oxychloride was distilled off and a 10% sodium hydroxide aqueous solution added under ice cooling. The mixture was extracted with methylene chloride, then was washed with a saturated aqueous solution of potassium bicarbonate and saturated saline and dried over anhydrous magnesium sulfate. The solvent was distilled off and the crude product obtained was purified by silica gel column chromatograph (hexane:ethyl acetate=6:1) to obtain 598 mg of the above-identified compound (yield 43%).

Example 26

Synthesis of 3,8-Dichloro-4,5-dihydro-4-(4-(4-(2-pyridyl)-1,2,3,6-tetrahydropyridin-1-yl)butyl)-1,4-benzoxazepin-5-one 200 mg of the compound of Example 25 was dissolved in 5 ml of DMF, 120 mg (1.2 equivalents) of 4-(2-pyridyl)-1,2,3,6-tetrahydropyridine, 187 mg (2 equivalents) of sodium iodide, and 0.17 ml (2 equivalents) of triethylamine were added, and the resultant mixture was stirred at 90° C. for 18 hours. The resultant mixture was processed and purified in the same way as Example 21 to obtain 117 mg of the above-identified compound (yield 43%). Note that a fumarate can be obtained by converting to a fumarate by an ordinary method, then recrystallizing from a mixed solvent of methanol and ether.

Example 27

Synthesis of 3,8-Dichloro-4,5-dihydro-4-(4-(4-(2-pyridyl)piperidin-1-yl)butyl)-1,4-benzoxazepin-5-one 200 mg of the compound of Example 25 was dissolved in 5 ml of DMF, 149 mg (1.2 equivalents) of 4-(2-pyridyl) piperidine hydrochloride, 187 mg (2 equivalents) of sodium iodide, and 0.30 ml (3.5 equivalents) of triethylamine were added, and the resultant mixture was stirred at 90° C. for 20 hours. The resultant mixture was processed and purified in the same way as Example 21 to obtain 158 mg of the above-identified compound (yield 59%). Note that a fumarate can be obtained by converting to a fumarate by an ordinary method, then recrystallizing from a mixed solvent of methanol and ether.

Example 28

Synthesis of 3-Chloro-4,5-dihydro-4-(4-(4-(2-pyridyl)-1,2,3,6-tetrahydropyridin-1-yl)butyl)-1,4-benzoxazepin-5-one (Synthesis of Identical Substance as Example 22 by Different Method)

800 mg of the compound of Example 19 was dissolved in 20 ml of ethanol, 140 mg (2 equivalents) of sodium borohydride was added under ice cooling, then the result was agitated at room temperature for 10 minutes. Water was added and extraction was performed with ethyl acetate. The organic layer was washed with water and saturated saline, then was dried with anhydrous magnesium sulfate. The solvent was distilled off and the resultant crude product was refined with silica gel column chromatography (methylene chloride:methanol=30:1), to obtain the above-referenced compound in an amount of 600 mg (yield of 81%).

TABLE 7

| Ex. | Chemical structure | m.p. (recrystallization solvent) | IR (cm⁻¹) | NHR (δppm) | | MS/elementary analysis |
|---|---|---|---|---|---|---|
| 19 | 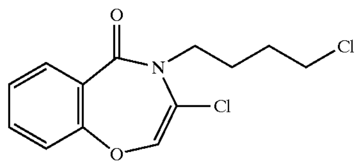 | | 2956 1704<br>1614 1605<br>1574 1538<br>1479 1236<br>(NaCl) | 7.86–7.89 (1H, m).<br>7.22–7.26 (1H, m).<br>6.73 (1H, s).<br>3.57–3.60 (2H, m). | 7.43–7.47 (1H, m).<br>7.02 (1H, d, J=8 Hz).<br>3.94 (2H, t, J=6 Hz).<br>1.86–1.89 (4H, m).<br>(COCl₂) | |
| 20 | 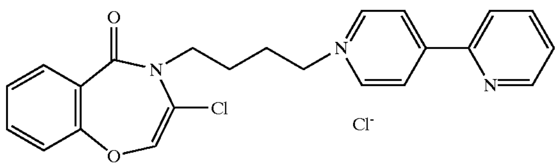 | | 3445 3008<br>1642 1603<br>1561 1475<br>1456 1342<br>1177 (KBr) | 9.21 (2H, d, J=7 Hz).<br>8.81 (2H, d, J=7 Hz).<br>8.11 (1H, d, l, J=2 Hz, 8 Hz).<br>7.77 (1H, dd, J=2 Hz, 8 Hz).<br>7.66 (1H, dd, J=4 Hz, 8 Hz).<br>7.58 (1H, dl, J=2 Hz, 8 Hz).<br>7.14 (1H, d, J=7 Hz).<br>4.71 (2H, t, J=7 Hz).<br>2.01–2.12 (2H, m). | 8.87 (1H, d, J=4 Hz).<br>8.44 (1H, d, J=8 Hz).<br>7.33 (1H, t, J=8 Hz).<br>7.10 (1H, s).<br>3.87 (2H, t, J=7 Hz).<br>1.65–1.71 (2H, m).<br>(DNSO-d₂) | |
| 21 | 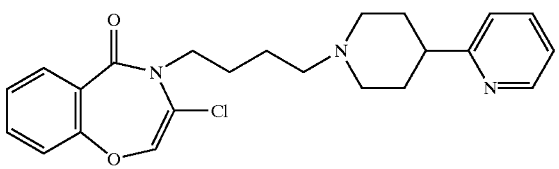 | 158–161° C. (2) (acetone) | 3428 2946<br>2672 1648<br>1540 1454<br>1378 1330<br>1241 (KBr)<br>(2) | 9.71 (1H, br).<br>7.89–7.91 (1H, m).<br>7.60 (1H, l, J=8 Hz).<br>7.14–7.18 (2H, m).<br>3.55–3.58 (2H, m).<br>2.04–2.15 (4H, m). | 8.55–8.59 (1H, m).<br>7.79 (1H, d, J=8 Hz).<br>7.31–7.40 (3H, m).<br>3.84–3.87 (2H, m).<br>2.95–3.18 (5H, m).<br>1.68–1.89 (4H, m).<br>(2) (DNSO-d₂) | FAB-Mass<br>412 (M + H)* |
| 22 | 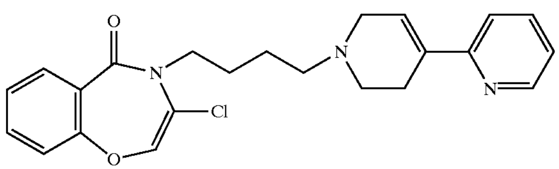 | 145–147° C. (2) (MeOH-acetone) | 3416 2928<br>2695 1652<br>1604 1560<br>1455 1381<br>1340 1198<br>(2) (KBr) | 10.74 (1H, br).<br>7.95–7.97 (1H, m).<br>7.70–7.72 (1H, m).<br>7.42–7.41 (1H, m).<br>7.14–7.17 (2H, m).<br>4.03–4.08 (1H, m).<br>3.64–3.67 (1H, m).<br>2.91–2.93 (2H, m).<br>1.70–1.75 (2H, m). | 8.61–8.63 (1H, m).<br>7.79 (1H, dd, J=2.8 Hz).<br>7.60 (1H, d, J=8 Hz).<br>7.34 (1H, l, J=8 Hz).<br>6.74–6.76 (1H, m).<br>3.84–3.87 (3H, m).<br>3.21–3.25 (3H, m).<br>1.84–1.86 (2H, m).<br>(2) (DMSO-d₂) | FAB-Mass<br>410 (M + H)* |

(2) Hydrochloride indicated as (2).

TABLE 8

| Ex. | Chemical structure | m.p. (recrystallization solvent) | IR (cm⁻¹) | NMR (δppm) | MS/elementary analysis |
|---|---|---|---|---|---|
| 23 | (structure: 3-chloro-4-(4-bromobutyl)-benzoxazepinone) | | 2958, 1640, 1479, 998 (NaCl) | 7.82–7.84 (1H, m), 7.17–7.21 (1H, m), 6.38 (1H, s), 3.47 (2H, t, J=7 Hz), 1.82 (3H, s) | |
| 24 | (structure with 2-pyridyl-tetrahydropyridine and Me-benzoxazepinone) | 165–168° C. (1) (acetone-Et₂O) | 2934, 1684, 1457, 1350, 1209 (1) | 8.51 (1H, d, J=5 Hz), 7.46–7.53 (2H, m), 7.05 (1H, dd, J=8 Hz), 6.60 (4H, s), 3.72–3.78 (2H, m), 2.70–2.73 (2H, m), 1.57–1.61 (4H, m) | 7.68–7.75 (2H, m), 7.20–7.25 (2H, m), 6.66 (1H, s), 6.56 (1H, s), 3.19–3.23 (2H, m), 2.50–2.59 (4H, m), (1) (DMSO-d₃) | FAB-Mass 390 (M + H)* |
| 25 | (structure: 3-chloro-N-(4-chlorobutyl)-7-chloro-benzoxazepinone) | | 1649, 1499, 1274 (CHCl₃) | 7.82 (1H, d, J=8 Hz), 7.06 (1H, d, J=2 Hz), 3.89–3.96 (2H, m), 1.82–1.99 (4H, m) | 7.23 (1H, dd, J=8 Hz, 2 Hz), 6.71 (1H, s), 3.55–3.61 (2H, m), (CDCl₃) | |
| 26 | (structure with 2-pyridyl-tetrahydropyridine and 3-chloro-7-chloro-benzoxazepinone) | 167–170° C. (1) (MeOH—Et₂O) | 3432, 1660, 1567, 1414, 1331, 1201 (1) | 8.51 (1H, d, J=4 Hz), 7.73 (1H, t, J=8 Hz), 7.40 (1H, d, J=9 Hz), 7.21 (1H, t, J=6 Hz), 6.62 (4H, s), 3.85 (2H, t, J=7 Hz), 2.70–2.77 (2H, m), 1.64–1.73 (2H, m) | 7.80 (1H, d, J=8 Hz), 7.51 (1H, d, J=8 Hz), 7.30 (1H, s), 7.12 (1H, s), 6.62 (4H, s), 3.19–3.25 (2H, m), 3.52–2.63 (4H, m), 1.53–1.64 (2H, m), (1) (DMSO-d₃) | FAB-Mass 444 (M + H)* |
| 27 | (structure with 2-pyridyl-piperidine and 3-chloro-7-chloro-benzoxazepinone) | 161–164° C. (1) (MeOH—Et₂O) | 3427, 1662, 1569, 1436, 1243 (1) | 8.48 (1H, d, J=4 Hz), 7.69 (1H, t, J=4 Hz), 7.30 (1H, d, J=2 Hz), 7.18 (1H, t, J=4 Hz), 6.59 (4H, s), 3.06 (2H, d, J=10 Hz), 2.45–2.55 (2H, m), 1.76–1.86 (4H, m), 1.53–1.61 (2H, m) | 7.80 (1H, d, J=8 Hz), 7.41 (1H, dd, J=2 Hz, 8 Hz), 7.25 (1H, d, J=8 Hz), 7.13 (1H, s), 3.85 (2H, t, J=7 Hz), 2.68–2.72 (2H, m), 2.14–2.25 (2H, m), 1.62–1.68 (2H, m), (1) (DMSO-d₃) | FAB-Mass 446 (M + H)* |

(1) Fumarate indicated as (1).

Due to the development of the present method, it is possible to obtain 2,4'-dipyridyl derivatives with a good yield, easily, in just a single process, compared with the conventionally known methods. Further, it becomes possible to separate and purify just 2,4'-dipyridyl derivative easily from a dipyridyl isomer mixture. This is a novel method of production useful for a 2,4'-dipyridyl derivative. Further, it is possible to use this method to easily produce benzoxazepine derivatives and its salts.

What is claimed is:

1. A method of producing a 2,4'-dipyridyl compound having the formula (II):

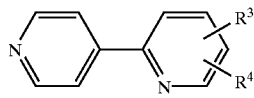

wherein $R^3$ and $R^4$ each represents a hydrogen atom, comprising reacting a 2-halopyridine compound having the formula (I):

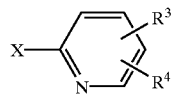

wherein X represents a halogen atom and $R^3$ and $R^4$ are the same as defined above with 4-halopyridine using a nickel complex catalyst in the presence or absence of a tetraalkylammonium halide to cause a coupling reaction therebetween; and separating the 2,4'-dipyridyl compound by:
dissolving a mixture of dipyridyl compound isomers containing a 2,4'-dipyridyl compound having the formula (II) in an organic solvent;
followed by insolubilizing and
adding a copper sulfate solution to remove byproducts as copper sulfate salts, wherein said byproducts include a 2,2'-dipyridyl compound and a 4,4'-dipyridyl compound.

2. A method of producing a 2,4'-dipyridyl compound as claimed in claim 1, wherein the nickel complex catalyst is a dihalide containing bivalent nickel catalyst selected from the group consisting of $NiCl_2(PPh_3)_2$, $NiBr_2(PPh_3)_2$, $NiI_2(PPh_3)_2$, $NiCl_2[Ph_2P(CH_2)_2PPh_2]$ and $NiCl_2[Ph_2P(CH_2)_3PPh_2]$.

3. The method according to claim 1, wherein the nickel complex catalyst is used in an amount of 10 to 50 mol % based on the 2-halopyridine compound and 4-halopyridine.

4. The method according to claim 2, wherein zinc is used in combination with the nickel complex catalyst.

5. The method according to claim 4, wherein zinc is used in an amount of about 1 to 4 equivalents of the 2-halopyridine compound and 4-halopyridine.

6. The method according to claim 1, wherein a tetraalkylammonium halide is present and used in an amount of about 0.1 to 3 equivalents of the 2-halopyridine compound and 4-halopyridine.

7. The method according to claim 6, wherein, for the tetraalkylammonium halide,
the alkyl group is ethyl or n-butyl, and
the halide is iodide or bromide.

8. The method according to claim 1, wherein the molar ratio of the 2-compound and the 4-halopyridine is 4:1 to 1:4.

9. The method according to claim 1, wherein the 2-halopyridine and 4-halopyridine compound are a 2-chloropyridine compound and a 4-chloropyridine compound, respectively.

10. The method according to claim 1, wherein the concentration of the ate solution used to produce the copper sulfate salts is 0.1M to 0.2M.

* * * * *